United States Patent [19]

Levy et al.

[11] Patent Number: 5,833,658
[45] Date of Patent: Nov. 10, 1998

[54] CATHETERS FOR THE DELIVERY OF SOLUTIONS AND SUSPENSIONS

[76] Inventors: Robert J. Levy, 2241 Belmont, Ann Arbor, Mich. 48104; Steven Goldstein, 608 Green Rd., Ann Arbor, Mich. 48105

[21] Appl. No.: 649,900

[22] Filed: Apr. 29, 1996

[51] Int. Cl.$^6$ .................................................. A61M 29/00
[52] U.S. Cl. ............................. 604/96; 606/192; 606/108
[58] Field of Search .......................... 604/96, 194, 103, 604/97, 52, 101; 606/192, 196, 108

[56] References Cited

U.S. PATENT DOCUMENTS

| | | |
|---|---|---|
| 4,490,421 | 12/1984 | Levy . |
| 4,824,436 | 4/1989 | Wolinsky . |
| 4,944,745 | 7/1990 | Sogard et al. . |
| 5,002,556 | 3/1991 | Ishida et al. . |
| 5,049,132 | 9/1991 | Shaffer et al. . |
| 5,059,178 | 10/1991 | Ya . |
| 5,087,244 | 2/1992 | Wolinsky et al. . |
| 5,328,471 | 7/1994 | Slepian . |
| 5,397,307 | 3/1995 | Goodin ...................................... 604/96 |
| 5,558,642 | 9/1996 | Schweich, Jr. et al. ................... 604/96 |

OTHER PUBLICATIONS

Fernandez–Ortiz, Antonio et al., 1994, "A New Approach for Local Inravascular Drug Delivery," *Circulation* 89:1518–1522.

Gonschlor, Peter, et al., JACC Feb. 1994:188A:891–34.

Hong, Mun K. et al., 1993, "Feasibility and Drug Delivery Efficiency of a New Balloon Angioplasty Catheter Capable of Performing Simultaneous Local Drug Delivery," *Coronary Artery Disease* 4:1023–1027.

McKay, Raymond G. et al., 1994, "Treatment of Intracoronary Thrombus With Local Urokinase Infusion Using a New, Site–Specific Drug Delivery System: The Dispatch™ Catheter," *Catheterization and Cardiovascular Diagnosis* 33: 181–188.

Robinson, Keith A., et al. JACC Feb. 1994:188A:891–35.

Wilinsky et al., 1990, "Use of a Perforated Balloon Catheter to Deliver Concentrated Heparin Into the Wall of the Normal Canine Artery," *J. Am. Coll. Cardiol.* 15:475–481.

Wilinsky et al., 1991, "Direct Intraarterial Wall Injection of Microparticles Via a Catheter: A Potential Drug Delivery Strategy Following Angioplasty," *Am. Heart J.* 122:1136–1140.

*Primary Examiner*—Michael Powell Buiz
*Assistant Examiner*—Kevin Truong
*Attorney, Agent, or Firm*—Pennie & Edmonds LLP

[57] ABSTRACT

The present invention provides single balloon infusion catheters that provide an infusion chamber between a body lumen and the catheter balloon when the catheter balloon is inflated. High concentrations of pharmaceutical formulations and other liquids and solutions can be delivered into the infusion chamber under low pressure for local infusion therapy. Optionally, the catheters permit fluids such as blood to continue flowing through the body lumen during infusion therapy.

7 Claims, 6 Drawing Sheets

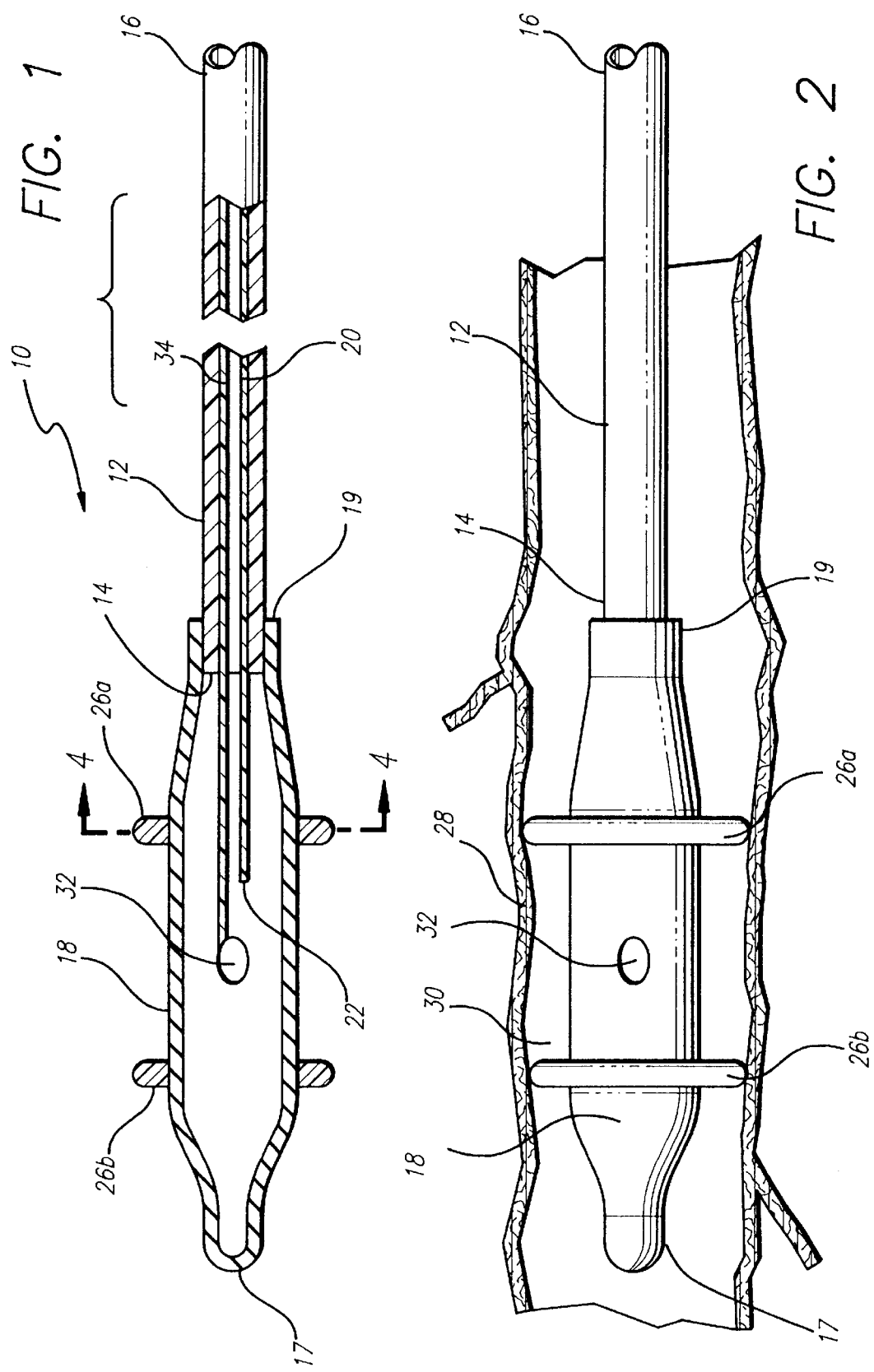

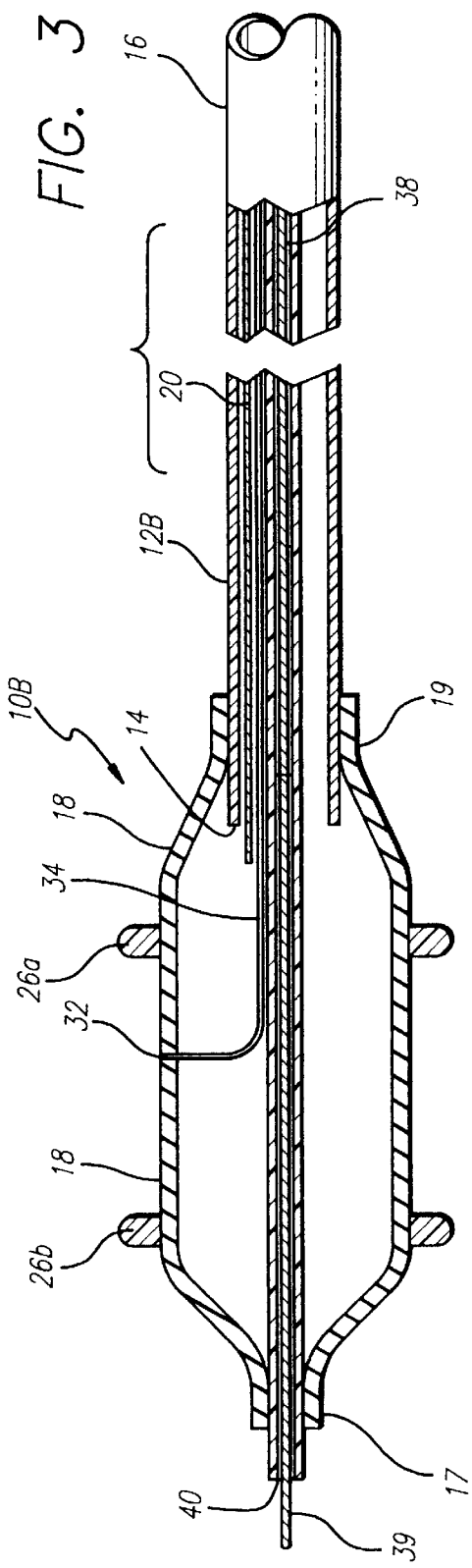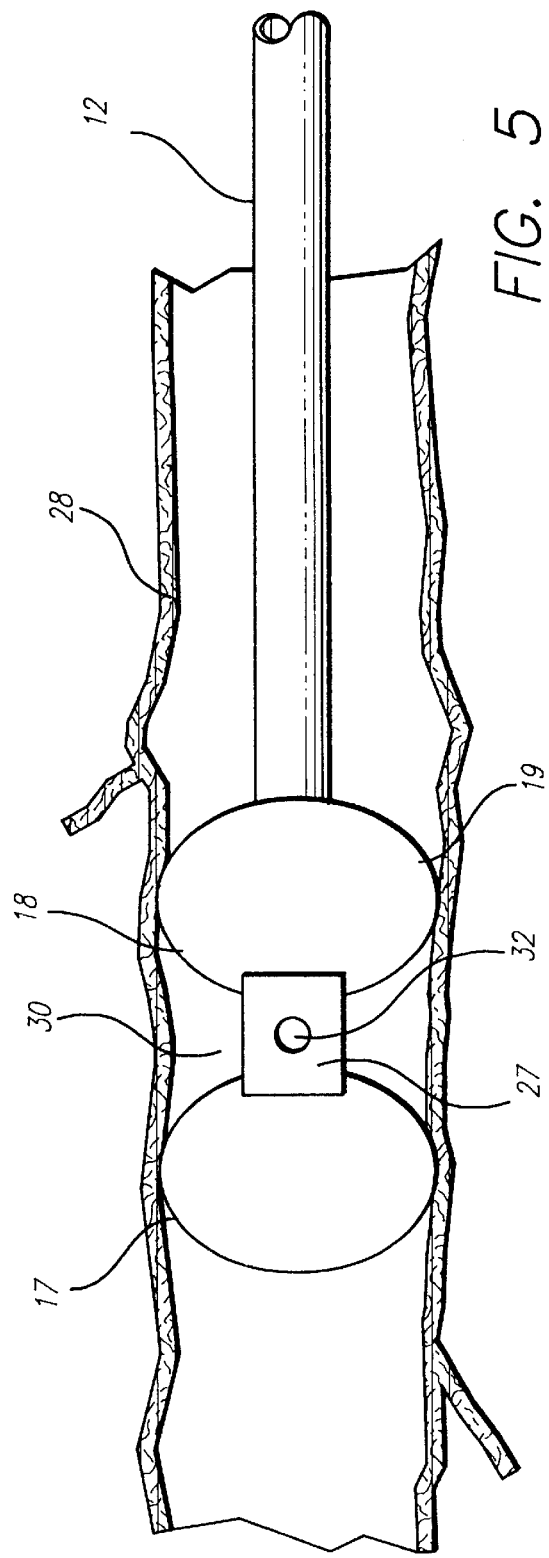

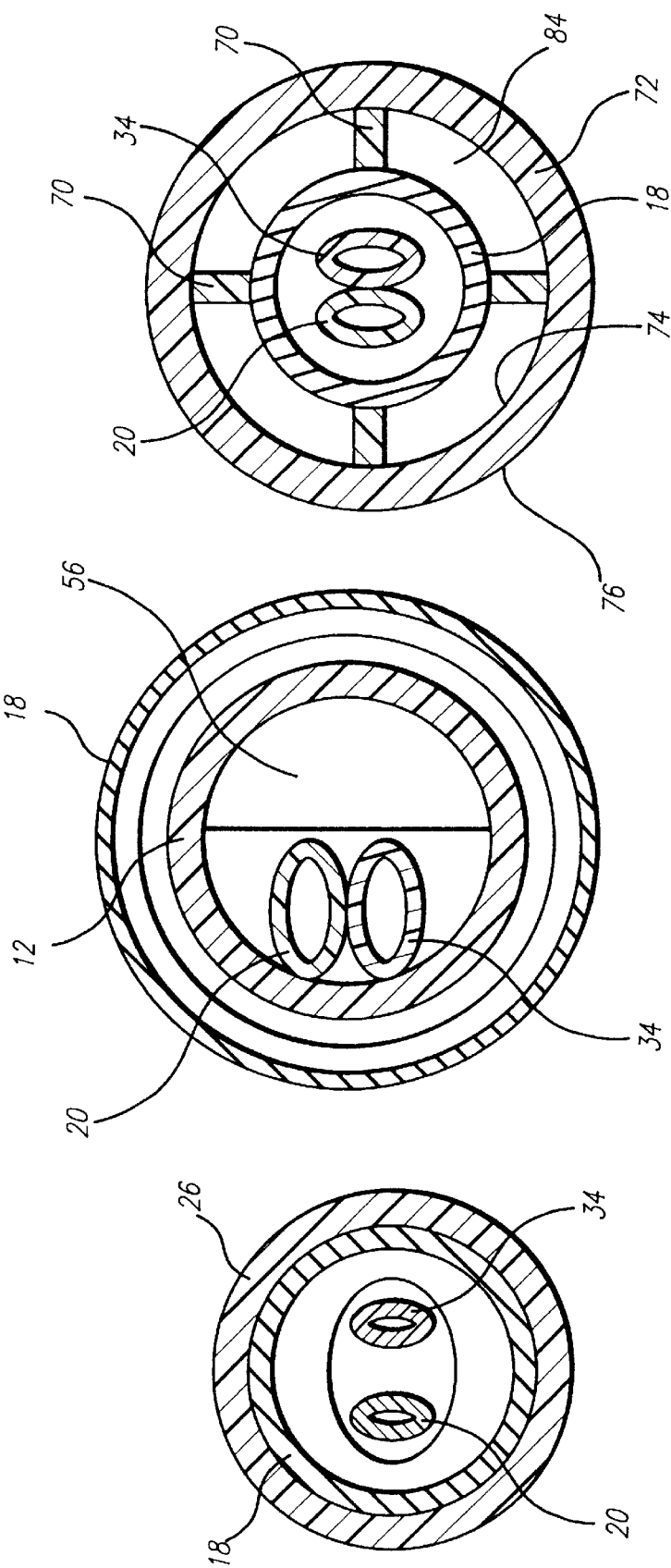

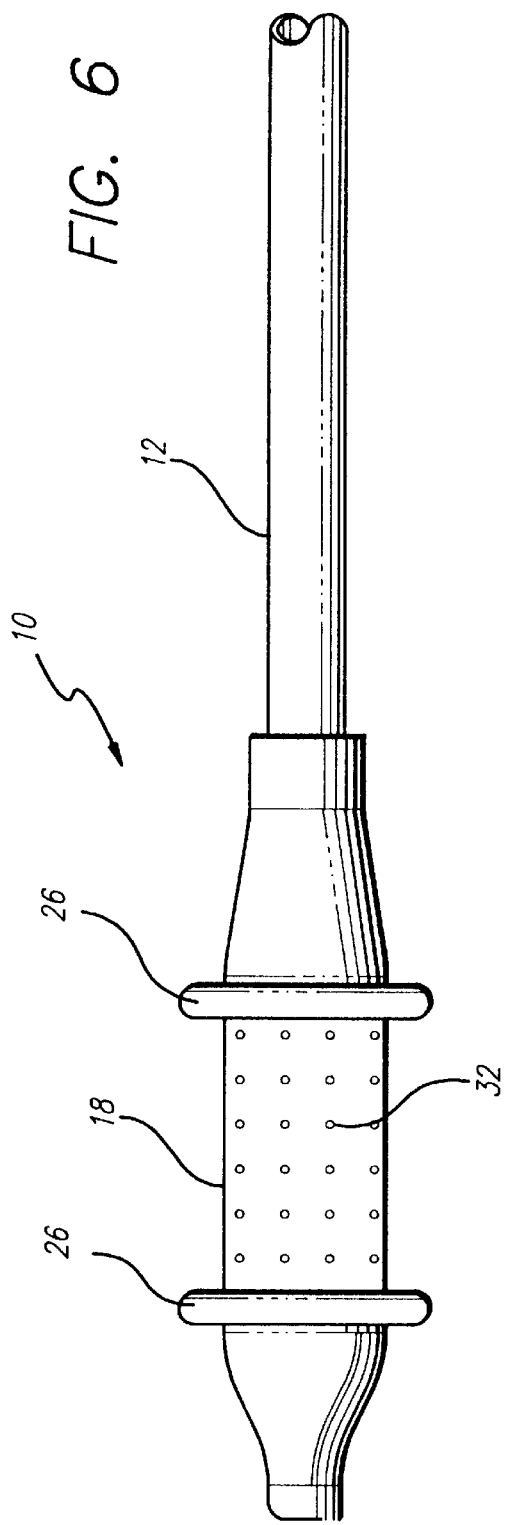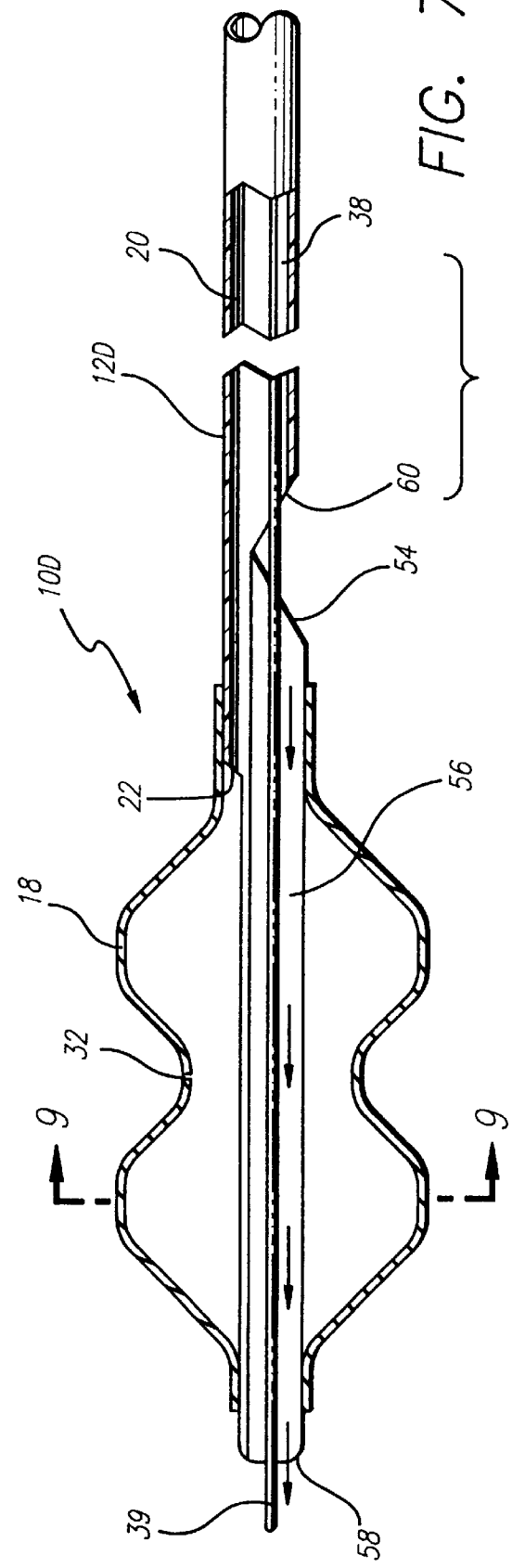

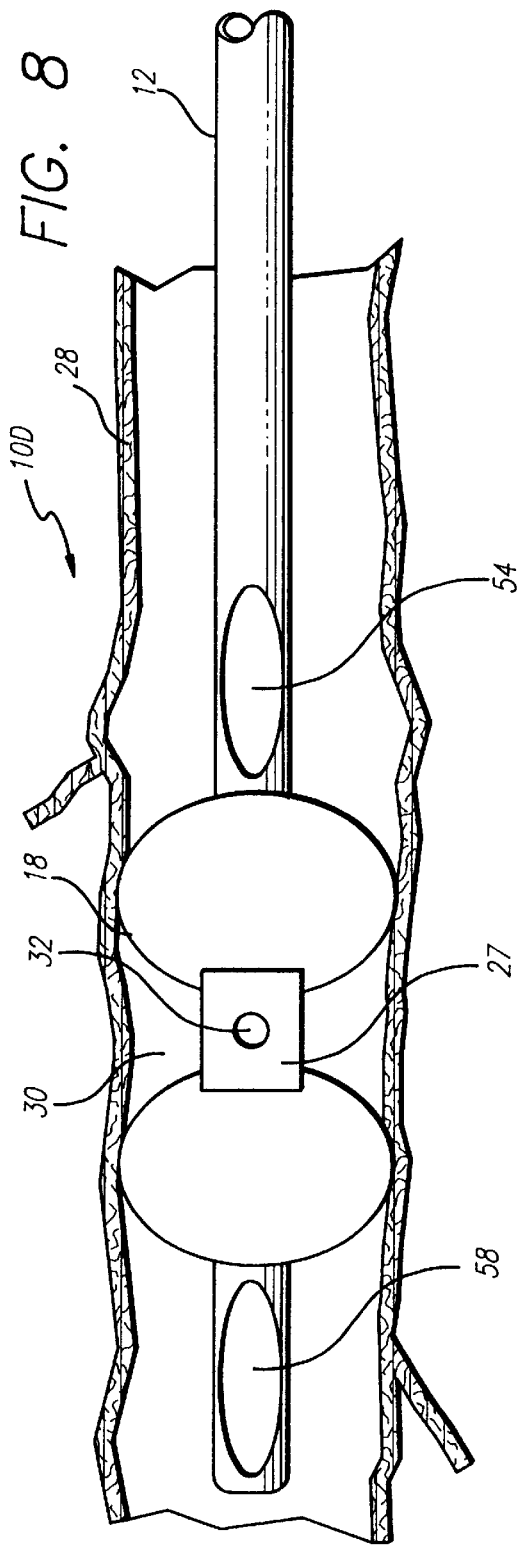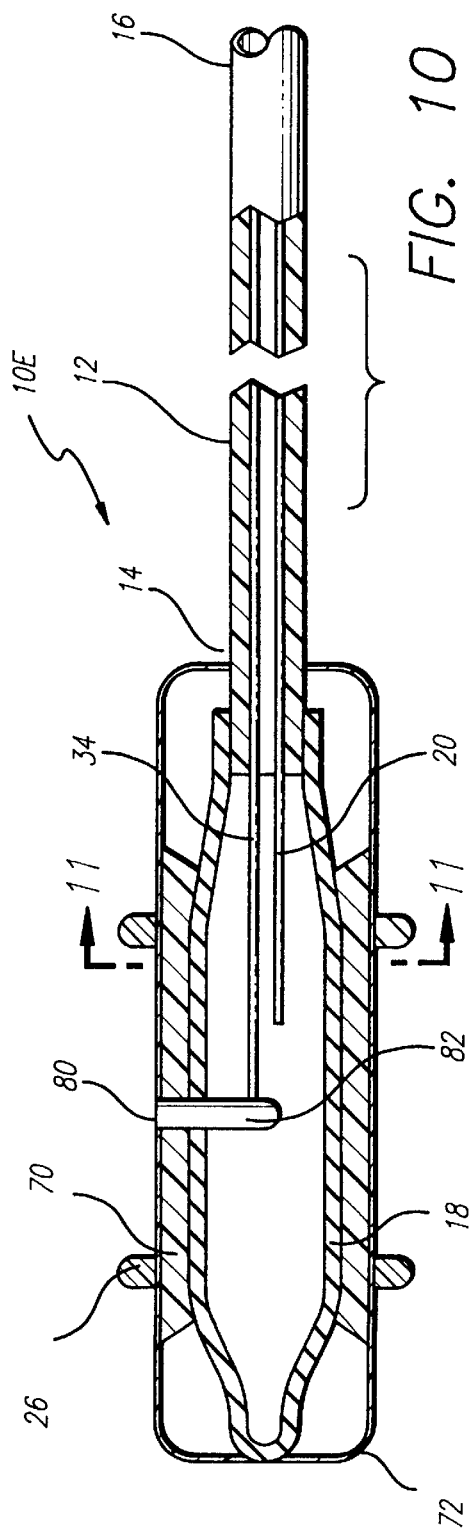

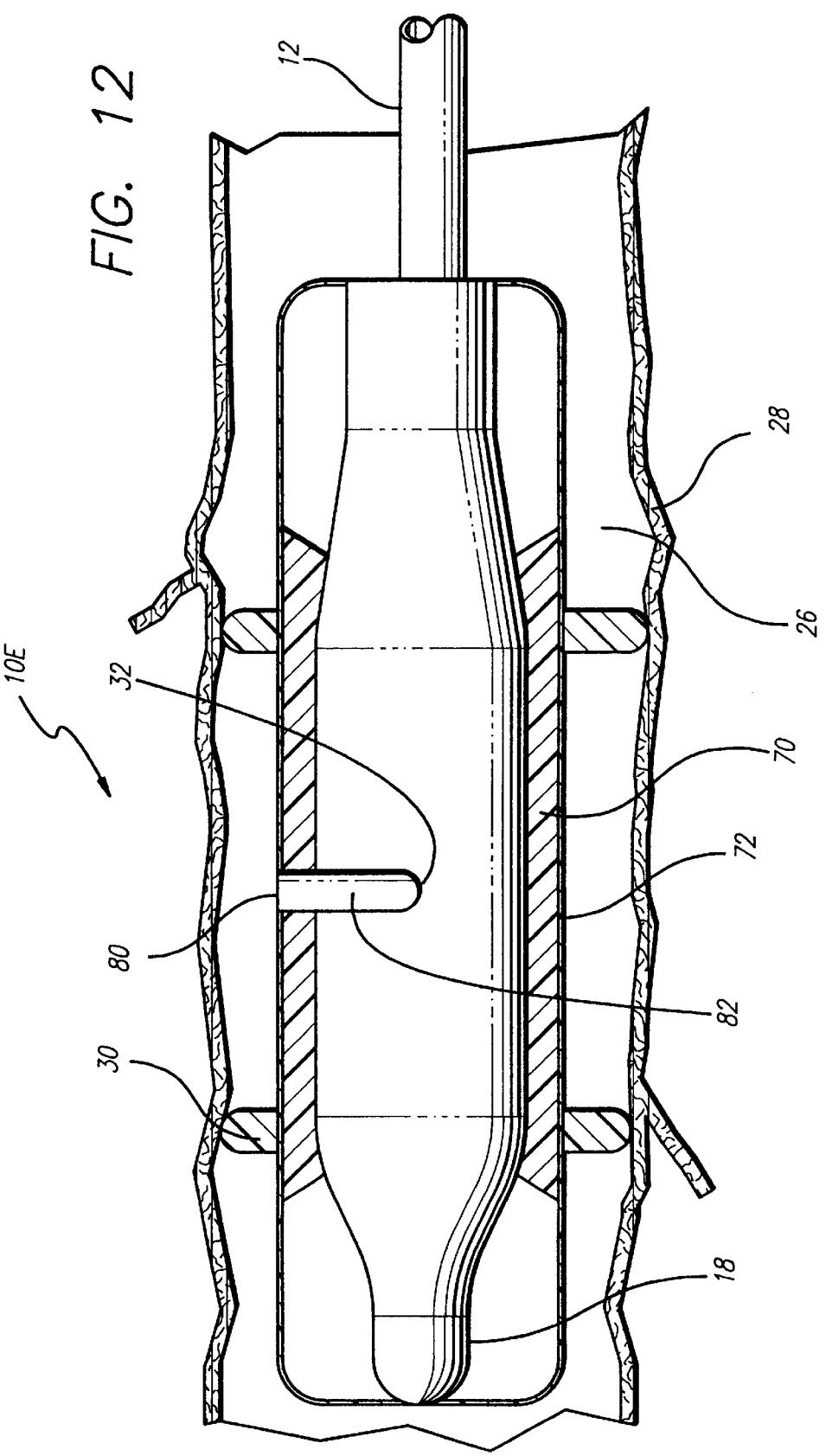

CATHETERS FOR THE DELIVERY OF SOLUTIONS AND SUSPENSIONS

INTRODUCTION

The present invention relates to single balloon drug infusion catheters for locally delivering liquids, particularly therapeutic pharmaceutical formulations, solutions and/or suspensions, into a body lumen, particularly a patient's vasculature. When inflated, the catheters of the invention create a chamber into which high concentrations of therapeutic and other agents may be infused under low pressure into a body lumen, particularly an artery or vein, with minimal contact between the catheter and vessel wall, thereby minimizing vessel injury. The single balloon catheters of the invention also permit infusion of liquids into highly branched arterial and/or venous regions. Optionally, the catheters allow blood to continue flowing through the patient's vasculature during infusion therapy.

BACKGROUND OF THE INVENTION

Balloon angioplasty has become a widely used alternative to coronary bypass surgery to open clogged arteries. More than 300,000 interventional cardiac catheterizations such as balloon angioplasty were performed in the United States in the past year alone. In this non-operative procedure, an inflatable catheter is used to improve the blood flow in patients with arterial disease.

Briefly, a catheter having an inflatable balloon at its distal end is inserted into an artery and positioned at the coronary stenotic zone using fluoroscopic control. The balloon at the distal end of the catheter is inflated under pressure for a short time and then deflated. The expanded balloon literally blows open the stenotic zone, increasing the luminal diameter of the stenotic artery. The inflation cycle is usually repeated several times to achieve satisfactory results. Luminal increases of stenotic vessels of at least 20% can be achieved using this method.

Restenosis, the rapid reblockage of coronary arteries following balloon angioplasty and other interventional cardiac catheterizations, occurs in thirty to fifty percent of all patients within the first year following surgery (Schwartz et al., 1992, *J. Am. Coll. Cardiol.* 20:1284; Liu et al., 1989, *Circulation* 79:1374). Restenosis generally involves abnormal replication of vascular smooth muscle cells ("SMCs") in the vessel wall in response to injury caused by the initial interventional catheterization.

Often the only practical treatment for restenosis is to repeat the interventional catheterization treatment, which may cause further damage to the cell wall and the need for even further angioplasty treatments. Thus, while interventional catheterizations such as balloon angioplasty have been one of the major advancements in the treatment of clogged arteries, their long term efficacy is limited by the onset of restenosis.

Recently, drug infusion catheters have been increasingly used for interventional cardiac catheterizations. These catheters allow local delivery of drugs useful to treat or prevent restenosis to the area being catheterized. Drug infusion catheters have also been used to perfuse many different types of arterial and venous vascular beds. Regional perfusion using this approach has been utilized in a variety of cardiovascular diseases, cancer chemotherapy, local infusion of antibiotics, local infusion of thrombolytic agents, and administration of X-ray and radionuclide contrast agents. Venous infusions have included novel drug administration in some cases such as the so-called retrovenous perfusion approach utilized in perfusing the myocardial circulation.

Ideally, catheters for locally delivering therapeutic and other agents should achieve sustained high local concentrations of therapeutic agents without causing systemic toxicity or undesirable side effects associated with systemic doses sufficient to obtain similar local concentrations. The catheter should produce little or no additional vascular trauma beyond that produced by the initial angioplasty or other revascularization procedure, as studies indicate that the extent of restenosis is related to the degree of arterial injury. Other desirable features include an ability to achieve high sustained local concentrations of therapeutic agents in highly branched vascular regions with loss of infusate to side branches, an ability to apply the infusion therapy for prolonged periods of time without causing significant downstream ischemia or thrombosis, and ease of use and manufacture.

Several catheters have been designed which attempt to meet these goals. However, these catheters are not well suited for drug infusions due to their design and flow characteristics. These catheters may cause arterial injury as a result of direct contact between the catheter balloon and the arterial wall, highly pressurized jet-streamed delivery of drugs, or combinations of these mechanisms. Other disadvantages include an inability to achieve sustained high local concentrations of therapeutic agents, significant localized tissue anemia, a condition called ischemia, or thrombosis downstream of the catheter due to obstruction of arterial blood flow by the catheter balloon and an inability to deliver drugs to highly branched vascular regions. Furthermore, many of the catheters are difficult to use and complex to manufacture.

The most commonly used drug infusion catheters are single balloon drug infusion catheters. One such catheter is described in U.S. Pat. No. 5,087,244 to Wolinsky. The catheter includes a thin walled flexible balloon having numerous small holes through which drug is infused. In practice, the balloon is inflated so that it contacts the vessel wall. Medication is then pumped into the balloon at a pressure sufficient to cause a thin film of medication to spread between the balloon and the vessel wall, and to force infused medication into the vessel wall (Wolinsky et al., 1990, *J. Am. Coll. Cardiol* 15:475–481; Wolinsky et al., 1991, *Am. Heart J.* 122:1136–1140). The depth of infusate penetration correlates with the duration and pressure of infusion.

Currently available single balloon drug infusion catheters suffer from several of the disadvantages previously discussed. This type of catheter may cause significant arterial trauma where the catheter balloon contacts the artery wall or from high-pressure jet-spray delivery of infusate through the numerous wall holes into the artery wall. Other disadvantages include an inability to achieve high local drug concentrations absent concomitant high systemic concentrations for agents that are not rapidly absorbed by the vessel wall, an inability to provide prolonged infusion therapy absent ischemia or thrombosis downstream of the balloon, and an inability to deliver infusate into branched vascular regions without loss of medication down side branches.

Another type of drug infusion catheter commonly in use is a flow-through drug infusion catheter. The best known drug infusion catheter in use now is manufactured by SciMed Life Systems Inc. and is sold under the tradename Dispatch™ Catheter. The Dispatch™ Catheter has an outer coil-shaped balloon that, when inflated, provides a series of spaces between the coils into which therapeutic agents may be infused. Blood continues to flow through the vessel during the infusion therapy via a central lumen, allowing prolonged contact of the infusate with the vessel wall.

Disadvantages of the Dispatch™ Catheter include significant vascular trauma where the multiple inflation coils contact the vessel wall and an inability to achieve sustained high local concentrations of therapeutic agents to branched vascular regions.

Double balloon drug infusion catheters are also fairly commonly employed. One such double balloon catheter is described in U.S. Pat. No. 4,824,436 to Wolinsky. Generally, the double balloon catheter has a main catheter body, a first balloon positioned at the distal end of the catheter and a second balloon positioned about 10–50 mm proximal to the first balloon. The main catheter body portion located between the two balloons has a small hole through which medication can be infused. Recent models include a perfusion lumen that permits blood to continue flowing through the vessel during infusion therapy (SciMed Life Systems, Inc.)

In practice, once the catheter is positioned within an artery, the two balloons are inflated with fluid until they contact the artery wall, forming a chamber between the artery wall and the main catheter body. Medication is then delivered into the chamber.

While the double balloon catheter design decreases the arterial area that is contacted during infusion therapy compared to the above-described catheters, double balloon catheters do not permit sustained high local concentrations of therapeutic agents at branched vascular regions. Additionally, double balloon catheters are difficult to use and expensive to manufacture due to their complex design.

As is evident from the above discussion, there remains a need in the art for drug infusion catheters that achieves all of the goals of successful drug infusion therapy. Specifically, there remains a need in the art for drug infusion catheters that: (i) permit local delivery of high sustained concentrations of therapeutic or other agents without causing toxicity or undesirable side effects associated with systemic doses sufficient to achieve similar local concentrations; (ii) induce minimal vascular trauma during infusion therapy; (iii) permit infusion of high local concentrations of therapeutic agents to branched vascular regions; (iv) permit infusion therapy to be applied for prolonged periods without causing significant downstream ischemia or thrombosis; and (v) are easy to use and manufacture. These and other deficiencies in the art are therefore objects of the present invention.

SUMMARY OF THE INVENTION

These and other objects are accomplished by the present invention, which in one aspect provides single balloon infusion catheters for locally delivering liquids, particularly pharmaceutical formulations, solutions and/or suspensions, into a body lumen, particularly an artery or vein. When inflated, the single balloon catheters of the invention provide a chamber between the vessel wall and catheter into which high concentrations of therapeutic or other agents can be infused under low pressure. The catheters cause minimal vascular trauma and also permit infusion into branched vascular regions. Optionally, the catheters of the invention allow blood to continue flowing through a patient's vasculature during the infusion therapy, thereby permitting infusion therapy to be applied for extended periods of time without causing significant ischemia or thrombosis downstream of the catheter balloon.

In accordance with one illustrative embodiment, a single balloon catheter capable of forming an infusion chamber within a patient's vasculature is provided having an elongated flexible shaft with a balloon mounted on a distal portion of the shaft. The shaft has an inflation lumen extending from the proximal end of the shaft towards the distal end of the shaft, terminating with an opening within the balloon such that the inflation lumen is in communication with the balloon.

The balloon has a distal region and a proximal region spaced apart by a central region. When inflated, the distal and proximal regions have an outer diameter greater than the outer diameter of the central region. When the balloon is inflated within a patient's vasculature, the distal and proximal regions of the balloon contact the inner wall of the vessel, forming an infusion chamber bounded by the vessel and the balloon. The balloon also has an infusion port positioned to deliver liquids into the infusion chamber. Optionally, the balloon may have a plurality of infusion ports positioned to deliver liquids into the infusion chamber.

In accordance with another illustrative embodiment of the invention, a single balloon infusion catheter capable of forming an infusion chamber within a patient's vasculature is provided having an elongated flexible shaft with a balloon mounted on a distal portion of the shaft. The shaft has an inflation lumen as previously described. The shaft may optionally have an infusion lumen extending from the proximal end of the shaft to an infusion port on the balloon.

In an alternative embodiment, the shaft has a guidewire lumen extending from the proximal end of the shaft towards the distal end of the shaft. The guidewire lumen may receive a guidewire for facilitating positioning of the catheter within a patient's vasculature.

The balloon has annular spacers having an outer diameter larger than the outer diameter of the inflated balloon. The spacers contact the inner wall of a patient's vasculature when the balloon is inflated, forming an infusion chamber between the balloon and the vessel. The balloon also has one or a plurality of infusion ports for delivery of liquids into the infusion chamber, as previously described.

In accordance with yet another illustrative embodiment of the invention, a single balloon infusion catheter capable of forming an infusion chamber within a patient's vasculature is provided having a balloon mounted on a distal portion of an elongated flexible shaft, as previously described. The balloon has a constricting annulus or band that restricts a portion of the balloon from inflating. When inflation pressure is applied to the balloon, the balloon inflates around the constricting annulus, forming a bottle gourd shape. The portions of the balloon that inflate contact the vessel wall, forming an infusion chamber between the vessel and the balloon. The balloon also has one or a plurality of infusion ports positioned to deliver liquids into the infusion chamber, as previously described.

In use, a single balloon infusion catheter is positioned within an artery or vein, optionally with the aid of a guidewire. A liquid is flowed into the balloon under low pressure by way of the inflation lumen, causing the balloon to inflate. As the balloon inflates, an infusion chamber is formed between the balloon and the patient's vessel, as previously described.

Constant pressure may be applied to the balloon, optionally with the aid of a pressure gauge, causing liquid to flow through the infusion port(s) of the balloon into the infusion chamber. The liquid is delivered to the infusion chamber under low pressure to avoid injuriously spraying the wall of the patient's vessel. After liquid has been infused, the balloon is collapsed by aspirating through the inflation lumen, and the catheter is removed.

In another aspect, the present invention provides a single balloon infusion catheter capable of forming an infusion chamber within a patient's vasculature that permits blood to continue flowing through the vessel during infusion therapy. In accordance with one illustrative embodiment a single balloon flow-through catheter is provided that has a balloon mounted on a distal portion of an elongated flexible shaft, as previously described. The shaft further has a perfusion inlet positioned proximal to the balloon and a perfusion outlet positioned distal to the balloon. A perfusion lumen extends from the perfusion inlet to the perfusion outlet.

In use, the single balloon flow-through catheter is positioned within a vessel and the balloon is inflated, forming an infusion chamber into which liquids may be infused, as previously described. Blood enters the perfusion inlet, traverses through the perfusion lumen, exits the perfusion outlet and continues flowing through the vessel.

In another illustrative embodiment, a single balloon flow-through catheter is provided having a balloon mounted on a distal portion of an elongated flexible shaft, as previously described. The balloon has a plurality of radial struts spaced, preferably equally, about the balloon. The struts resemble fins extending radially from the balloon.

An elastic sleeve is disposed over the struts, coaxial with the longitudinal axis of the balloon. The struts space the sleeve radially from the balloon. The sleeve has at least two annular spacers positioned or juxtaposed over the struts. When the balloon is inflated, the struts force the elastic sleeve and the spacers to stretch. The spacers contact the wall of a patient's vessel, forming an infusion chamber between the outer surface of the elastic sleeve and the artery wall. A perfusion or flow-through space is formed between the inner surface of the elastic sleeve and the balloon. Thus, the elastic sleeve serves as a barrier between the infusion chamber and blood flowing through the patient's vessel.

The elastic sleeve also has an infusion outlet generally aligned with an infusion port on the balloon for delivery of liquids into the infusion chamber.

In use, once the catheter is positioned in the vessel the balloon is inflated by flowing a liquid through the inflation lumen into the balloon, as previously described. The catheter forms an infusion chamber and perfusion or flow-through space in the patient's vessel as described above. Liquid flows through the infusion tube and exits the infusion outlet into the infusion chamber. Blood continues to flow through the patient's vessel during the infusion therapy. After infusion of liquid the balloon is collapsed as previously described and the balloon removed.

In a final aspect, the invention relates to methods of performing infusion therapy. The methods generally involve positioning a single balloon infusion catheter in a body lumen, inflating the catheter to create an infusion chamber between the lumen wall and the catheter, as previously described, and delivering a liquid such as a pharmaceutical formulation or radiocontrast into the infusion chamber through the catheter.

FIGURES

FIG. 1 is a longitudinal cross-section of a catheter according to the invention;

FIG. 2 is a side view of the catheter of FIG. 1 shown placed within a branched artery with the balloon inflated;

FIG. 3 is a longitudinal cross-section of an alternative embodiment of a catheter of the invention including a guidewire lumen and guidewire;

FIG. 4 is a cross-section of the catheter of FIG. 1 through line A–A';

FIG. 5 is a side view of an alternative embodiment of a catheter according to the invention having a balloon with a constricting annulus, shown placed within an artery;

FIG. 6 is a side view an alternative embodiment of a catheter according to the invention having a plurality of infusion ports;

FIG. 7 is a longitudinal cross-section of an alternative embodiment of the invention including a flow-through perfusion lumen;

FIG. 8 is a side view of the catheter of FIG. 7 shown placed within an artery with the balloon inflated;

FIG. 9 is a cross-section of the catheter of FIG. 7 through line B–B';

FIG. 10 is a longitudinal cross-section of a catheter according to the invention having a flow-through strut design;

FIG. 11 is a cross section of the catheter of FIG. 10 through line C–C'; and

FIG. 12 is a side view of the catheter of FIG. 10 shown placed within an artery with the balloon inflated.

DETAILED DESCRIPTION OF THE INVENTION

Referring to FIG. 1, one illustrative embodiment of a single balloon infusion catheter 10 according to the present invention has an elongated flexible shaft 12 that may be formed from an any of a number of readily available non-toxic, flexible polymers as are known in the art. Suitable material include, by way of example and not limitation, polyolefins such as polyethylene or polypropylene and polyvinyl halides such as polyvinyl chloride or polyvinylidene chloride.

The dimensions of shaft 12 will depend on the intended application of the catheter, and will be readily apparent to those having ordinary skill in the art. By way of example, when the catheter is intended to be used in the coronary arteries shaft 12 may be of the order of 150 cm long and may have an outer diameter of about 0.05 to 0.2 cm.

Shaft 12 has a distal end 14 and a proximal end 16. An inflatable and deflatable balloon 18 having a distal end 17 and a proximal end 19 is mounted on the distal end 14 of shaft 12. Preferably, balloon 18 is bonded or affixed to shaft 12 so that it does not become dislodged during catheterization as is known in the art for balloon catheters.

Shaft 12 includes an inflation lumen 20 that extends from the proximal end 16 of shaft 12 and terminates with an opening 22 within balloon 18 such that inflation lumen 20 is in communication with balloon 18. Shaft 12 may also be formed to include an infusion lumen 34 that extends from the proximal end 16 of shaft 12 and terminates with an infusion port 32 on balloon 18.

The proximal end 16 of shaft 12 may have fittings (not shown) by which the inflation lumen 20 and/or infusion lumen 34 may be connected to a syringe or other pressure fluid and/or gas delivery devices.

Referring now to FIG. 3, an alternative embodiment of a catheter according to the invention is illustrated including a guidewire lumen and guidewire. Alternative catheter 10B has an elongated flexible shaft 12B, as previously described. Shaft 12B is formed to further include a guidewire lumen 38 that extends from the proximal end 16 of shaft 12 and terminates in an outlet 40 at the distal end 17 of balloon 18. Guidewire lumen 38 may be used to receive a guidewire 39 by which catheter 10 may be guided through a patient's vasculature to the site to be treated.

Balloon 18 may be formed from various polymeric materials and desirably has a thin, flexible, wall. Balloon 18 may be elastic or inelastic. When inelastic, balloon 18 will inflate to pre-defined dimensions so as to minimize the possibility of over-inflating the balloon and causing arterial injury. It is contemplated that several different sizes of inflated balloons may be necessary, depending on the application in which the catheter is to be used. The actual dimensions of the balloon will be readily apparent to those having skill in the art. By way of example, a catheter according to the invention adapted for use in coronary arteries may have a balloon about 1 cm or more long and a wall thickness of about 0.003 cm or less. A balloon having a wall thickness of 0.001 inch or less may be fabricated as described in U.S. Pat. No. 4,490,421 to Levy (incorporated herein in its entirety by reference).

When the balloon is relatively elastic, it is contemplated that balloon 18 will inflate to the dimensions appropriate for a particular application, as described above. Preferably, the balloon will not inflate to dimensions substantially larger than the vasculature of the patient being treated even under pressures as high as 2–5 atmospheres.

Suitable materials for forming balloon 18 are well known in the art and include, by way of example and not limitation, polyvinyl chloride, polyurethane, copolyesters, thermoplastic rubbers, silicone polycarbonate copolymers, ethylene-vinyl acetate copolymers, and the like.

As illustrated in FIG. 2, one of the main advantages of the catheters of the present invention is the formation of an infusion chamber 30 between catheter balloon 18 and vessel wall 28 upon inflation of balloon 18. Infusion chamber 30 permits local delivery of small volumes of highly concentrated solutions under low pressures.

Solution is delivered into infusion chamber 30 by way of infusion port 32 located on balloon 18. Infusion port 30 may be a small perforation in balloon 18 such that infusion chamber 30 is in communication with the interior of balloon 18 via infusion port 32. Alternatively, infusion port 32 may be connected to infusion lumen 34 such that infusion chamber 30 is in communication with infusion lumen 34.

In an alternative embodiment, illustrated in FIG. 6, balloon 18 may have a plurality of infusion ports 32 for infusion of solutions into chamber 30. The ports may be formed by a laser beam from an excimer laser having a wavelength of 248 or 308 nm, as described in U.S. Pat. No. 5,087,244 (incorporated herein in its entirety by reference), or by other means as are well known in the art.

Infusion port(s) 32 should be large enough to permit atraumatic infusion of liquids into infusion port 30. By atraumatic is meant delivery of liquid in such a fashion that the liquid does not forcefully spray against the vessel wall. Typically, infusion port(s) 32 will permit atraumatic infusion of liquids into infusion chamber 30 under about 0.1 to 5 atmospheres pressure and preferably under about 2 to 5 atmospheres pressure.

Different balloon designs may be employed to create infusion chamber 30 upon inflation of balloon 18. In one embodiment, illustrated in FIG. 2, balloon 18 has a proximal annular spacer 26a and a distal annular spacer 26b (collectively spacers 26) positioned such that when balloon 18 is inflated spacers 26 contact vessel wall 28, forming infusion chamber 30 between vessel wall 28 and balloon 18. Preferably, the distance between spacers 26 is small enough to permit infusion of solutions into vessels that are highly branched. Coronary arteries in particular are highly branched, with side branching arising every 2 to 6 mm. Thus, drug infused over a side branch would tend to rapidly run-off without perfusing the diseased arterial wall of interest.

Generally, the distance between spacers 26 is about 1.5 to 10 mm, preferably about 2 to 3 mm. However, appropriate spacing will be readily apparent to those having skill in the art, depending on the particular application.

Referring now to FIG. 4, spacers 26 have an outer diameter larger than the outer diameter of inflated balloon 18. Spacers 26 may be integral to balloon 18, or may be circumferentially mounted on balloon 18. Preferably, spacers 26 are affixed or bonded to balloon 18 so that they do not become dislodged when balloon 18 is inflated. Spacers 26 may be bonded to balloon 18 by any suitable means including, for example, epoxy.

One of the main features of spacers 26 is that they are elastic so that they stretch when balloon 18 is inflated. Suitably elastic spacers 26 may be formed from various elastic polymeric materials including, by way of example and not limitation, polyurethanes, silicone rubber, polyurethanesilicone copolymers, polyethylene, polyvinyl chloride, and other elastomers as will be apparent to those having ordinary skill in the art.

While the actual dimensions of spacers 26 will depend on the size of the vessel being catheterized, spacers 26 generally have a resting outer diameter that is smaller than the inner diameter of the vessel being catheterized so that contact with the vessel wall is minimized or avoided when the deflated catheter is guided through the artery. Spacers 26 may be tapered as illustrated in FIG. 2 to minimize the vessel area contacted when balloon 18 is inflated.

It is important that when balloon 18 is inflated, spacers 26 have an outer diameter that is larger than the outer diameter of inflated balloon 18, thereby forming infusion chamber 30 between balloon 18 and vessel 28 into which solutions may be easily and efficiently infused, while at the same time minimizing or preventing injurious contact between balloon 18 and vessel 28. Generally, spacers 26 will have an outer diameter of about 0.1 to 2 mm larger than the outer diameter of inflated balloon 18, preferably about 1 mm larger than the outer diameter of inflated balloon 18.

An important feature of spacers 26 is that they stretch and expand relatively easily under the pressures used to inflate balloon 18, so that spacers 26 do not appreciably restrict expansion of balloon 18 in the vicinity of spacers 26. The elastic resistance of spacers 26 will depend in large part on the materials used to construct spacers 26 and upon factors such as the width and thickness of the spacers. Generally, when balloon 18 is elastic, spacers 26 will be more elastic than balloon 18.

Additionally, spacers 26 are generally pliable or supple enough to form a seal between spacers 26 and vessel wall 28. In preferred embodiments spacers 26 are supple enough to provide a seal in vasculature regions containing plaque.

Referring now to FIG. 5, an alternative catheter of the invention capable of forming an infusion chamber 30 between vessel 28 and balloon 18 is provided. In alternative catheter 10C, balloon 18 has a constricting annulus 27 instead of spacers 26 for creating infusion chamber 30 upon inflation of balloon 18. Constricting annulus 27 has an outer diameter that is smaller than the outer diameter of inflated balloon 18. Preferably, constricting annulus 27 is positioned roughly in the center of balloon 18.

Constricting annulus 27 may be elastic or inelastic, and may be formed from any suitable materials such as, for example, the materials previously described for balloon 18.

Constricting annulus 27 may be integral to balloon 18, or may be circumferentially mounted on balloon 18. In a preferred embodiment, constricting annulus 27 is affixed or bonded to balloon 18 as previously described.

As illustrated in FIG. 5, infusion port(s) 32 may be placed within constricting annulus 27 for delivery of medication into infusion chamber 30.

When balloon 18 is elastic, constricting annulus 27 is preferably less elastic than balloon 18 so that constricting annulus 27 does not stretch appreciably when balloon 18 is inflated, forcing the proximal 19 and distal 17 ends of balloon 18 to inflate forming a bottle gourde shape. The distal 17 and proximal 19 ends of balloon 18 contact vessel wall 28, forming infusion chamber 30 as suggested in FIG. 5.

Optionally, constricting annulus 27 may be radiopaque to help guide the positioning of the catheter in a patient's vasculature.

The size of chamber 30 will depend in large part on the width of constricting annulus 27. Preferably, the width of constricting annulus 27 will be small enough to permit infusion therapy into vasculature regions that are highly branched. Generally, the width of constricting annulus 27 will be about 0.2 to 6 mm, preferably about 1 to 3 mm.

In use catheter 10 is guided to the area of the artery to be treated. Catheter 10 may be optionally advanced over guidewire 39 to aid the positioning of catheter 10 in the patient's vasculature. The catheter is preferably provided with one or more radiopaque marker bands by which the position of the catheter may be monitored under fluoroscopy to verify placement of the balloon in the region to be treated.

Once the balloon is positioned in the region to be treated, a syringe or other inflation device is operated to pressurize the catheter by flowing a pharmaceutical solution through inflation lumen 20 and into balloon 18, causing the balloon to inflate. As the balloon inflates, spacers 26 stretch and contact vessel wall 28, forming infusion chamber 30 as suggested in FIG. 2. Alternatively, distal end 17 and proximal end 19 of balloon 18 inflate around constricting annulus 27 forming infusion chamber 30 as suggested in FIG. 5. Medication flows through infusion port 32, spreading into infusion chamber 30, where it can proliferate through vasculature tissue.

Pressure may be applied continually at the inflation device (optionally fitted with a pressure gauge) to maintain a substantially constant pressure level and seal with the vessel wall as desired. While any pressure that will permit fluid to gently flow into infusion chamber 30 may be used, the range of pressures is anticipated to be about 1 to 5 atmospheres, preferably about 2 to 3 atmospheres.

The pressure and flow of medication will be continued for a predetermined time sufficient to achieve the desired penetration of medication into the vessel wall. Balloon 18 is then deflated by aspirating through inflation lumen 20 to cause the balloon to collapse, and the catheter removed.

Alternatively, once the balloon is positioned in the region to be treated, the syringe or other pressure device is operated to pressurize the catheter by flowing isotonic saline solution, plasma expanders, $CO_2$, etc. through inflation lumen 20 and into balloon 18, causing the balloon to inflate and form infusion chamber 30, as previously described. A constant pressure may be applied to the balloon to maintain a seal with the vessel, as previously described.

To apply medication, a syringe or other pressure device is then operated under low pressure to gently flow medication through infusion lumen 34 and out through infusion port 32. The medication will be applied at sufficiently low pressures so that the medication flows into chamber 30 without forcibly spraying vessel wall 28, as described above.

Flow of medication may be applied with constant pressure at the pressure device (optionally fitted with a pressure gauge). Following delivery of medication, balloon 18 may be collapsed as previously described, and the catheter removed.

Referring now to FIG. 7, an alternative catheter of the present invention is illustrated. Alternative catheter 10D permits blood to continue flowing through a patient's vasculature during infusion therapy. Blood flow-through or perfusion during catheterization allows medications to be applied for prolonged periods of time without causing tissue downstream of the balloon to become oxygen or nutrient-starved due to lack of blood. Perfusion also prevents downstream stasis and thrombosis.

Alternative catheter 10D has a balloon 18 mounted on an elongated flexible shaft 12D. Shaft 12D has an inflation lumen 20 in communication with balloon 18 and optionally, an infusion lumen connected to infusion port 32, as previously described for shaft 12. Shaft 12D further has perfusion inlet 54, perfusion lumen 56 and perfusion outlet 58. Perfusion inlet 54 is positioned proximate to balloon 18 and perfusion outlet 58 is positioned distal to balloon 18. In use, blood flows into perfusion inlet 54, traverses down perfusion lumen 56 and exits through perfusion outlet 58, as indicated by the arrows in FIG. 7.

Optionally, shaft 12D may be formed to have a guidewire lumen 38 for receiving guidewire 39. Guidewire lumen 38 extends from the proximal end of shaft 12D and terminates at distal opening 60, which is positioned adjacent to perfusion inlet 54. As illustrated in FIG. 7, guidewire 39 extends through perfusion channel 56 and out through perfusion outlet 58. Guidewire 39 may remain in place during infusion therapy or may be retracted.

In a preferred embodiment, perfusion inlet 54 is beveled at an angle with respect to the longitudinal axis of shaft 12 to allow easy entry of blood into perfusion lumen 56. Preferably, perfusion inlet 54 is beveled at a 30–60° angle with respect to shaft 12. The purpose of the beveled angle is to provide as unobstructed a flow path as possible for blood entering perfusion inlet 54 and perfusion lumen 56. Perfusion inlet 54 should be beveled in a fashion so as to provide shaft 12 with a relatively smooth profile to facilitate movement of alternative catheter 10D during insertion and removal.

Perfusion lumen 56 is sufficiently large so that balloon 18 can remain inflated for prolonged periods of time without causing significant ischemia stasis or thrombosis downstream from balloon 18. Preferably, perfusion lumen 56 has a diameter of about 3–8 mm when the balloon is inflated.

Referring now to FIG. 8, in use alternative catheter 10D, optionally advanced over guidewire 39, is guided to the area of the artery or vein to be treated, preferably with the aid of radiopaque markers as previously described. Once the balloon is positioned in the region to be treated, balloon 18 is inflated, forming infusion chamber 30 as previously described.

As blood flow through the artery becomes blocked, blood enters perfusion inlet 54, traverses through perfusion lumen 56 and exits via perfusion outlet 58 to continue flowing down the vessel. Medication is applied and the catheter is collapsed and removed as previously described. Since blood continues to flow through the patient's vasculature, the infusion therapy may be applied for prolonged periods of time.

It should be understood that while flow-through catheter 10D is illustrated with a balloon having a constricting annulus, balloons having spacers 26 as illustrated in FIG. 1 and FIG. 3, as well as any balloons capable of forming an infusion chamber as described herein, may also be used in flow-through catheter 10D.

Referring now to FIG. 10, an alternative single balloon flow-through catheter of the invention is provided. Alternative catheter 10E is substantially identical to catheter 10 except for the design of balloon 18.

Alternative catheter 10E has at least three radial struts 70 positioned about balloon 18. Struts 70 may be integral to balloon 18, or may be mounted on balloon 18. When mounted on the balloon, preferably, struts 70 are bonded or affixed to balloon 18 so that they do not become dislodged during the catheterization process. Struts 70 may be bonded or affixed to balloon 18 by any suitable means.

Struts 70 are positioned on balloon 18 such that a length of strut 70 aligns with a longitudinal axis of balloon 18. As illustrated in FIG. 11, struts 70 are preferably equally spaced about the cross-sectional circumference of balloon 18, resembling radially extending fins.

As illustrated in FIG. 12, the length of strut 70 that is affixed to balloon 18 may be incurvate to fit the shape of the balloon when the balloon is inflated.

Struts 70 may be elastic such that the length of strut 70 in contact with balloon 18 stretches as balloon 18 inflates. While elastic, struts 70 should also be substantially rigid and non-compressible so that struts 70 do not substantially compress or bend under the pressures used to inflate balloon 18. Suitable materials include, by way of example and not limitation, polyurethane, silicone and polyvinyl chloride.

The size of struts 70 will depend in large part on the dimensions of the vessel being catheterized. Typically, struts 70 will have a length approximately equal to the length of the balloon, and will extend about 1–4 mm radially from the balloon. Dimensions suitable for particular applications will be apparent to those having skill in the art.

Referring now to FIG. 11, a generally cylindrical or tubular elastic sleeve 72 having an inner surface 74 and an outer surface 76 is positioned over struts 70, coaxial with a longitudinal axis of balloon 18. Struts 70 space elastic sleeve 72 from balloon 18. Preferably, sleeve 72 is bonded or affixed to struts 70, as previously described.

Referring now to FIG. 12, elastic sleeve has annular spacers 26 as previously described. Spacers 26 are positioned or juxtaposed over struts 70, so that struts 70 also space spacers 26 from balloon 18. Spacers 26 may be integral to or circumferentially mounted on elastic sleeve 70. When mounted on the sleeve, preferably, spacers 26 are bonded or affixed to sleeve 72, as previously described.

Sleeve 72 is elastic in that it stretches as balloon 18 is inflated and struts 70 are pushed into sleeve 72. Sleeve 72 may be composed of any suitable elastic polymer as will be apparent to those having skill in the art.

Preferably, alternative catheter 10E, when deflated, has overall dimensions that allow the catheter to be positioned within a patient's vasculature without causing significant contact between the catheter and inner wall of the vessel.

Sleeve 72 has an infusion outlet 80 connected to infusion port 32 by way of infusion tube 82 for infusion of solutions into infusion chamber 30. Alternatively, infusion outlet 80 is connected to infusion lumen 34 (FIG. 10).

In use, single balloon flow-through catheter 10E is positioned within a patient's vasculature and inflated with a pharmaceutical solution or isotonic saline solution as previously described. As balloon 18 inflates, struts 70 force elastic sleeve 72 and spacers 26 to stretch radially. Spacers 26 contact vessel wall 28, forming infusion chamber 30 between vessel wall 28 and the outer surface of sleeve 70. Solution flows through infusion port 32 into infusion tube 80 and enters infusion chamber 30 via infusion outlet 80.

As illustrated in FIG. 11, inflation of balloon 18 also creates flow-through space 84, bounded by balloon 18 and the inner surface of sleeve 72. Blood continues to flow through flow-through space 84 during infusion therapy, permitting infusion for extended periods of time without causing significant ischemia stasis or thrombosis downstream of balloon 18.

The single balloon catheters of the invention provide myriad advantages over currently available catheters. The single balloon catheters of the invention permit easy and efficient formation of an infusion chamber between the catheter balloon and vessel wall into which high concentrations of therapeutic and other solutions may be infused under low pressures. The infusion chamber is formed merely by inflating the balloon.

Infusing solutions under low pressures into an infusion chamber provides significant advantages. First, infusing solutions under low pressure greatly reduces the incidence of vascular trauma caused by high pressure jet-spray delivery of solution against the vessel wall that is common with other single balloon infusion catheters.

Second, by use of spacers or a constricting annulus, the area of contact between the catheter and a patient's vessel is minimized compared to other single balloon catheters. Thus, the catheters of the invention reduce or minimize injurious vessel-catheter contact.

Third, the solution is retained in an infusion chamber rather than being continuously washed down the blood stream during infusion therapy. Thus, the catheters of the invention permit local delivery of small volumes of high concentrations of pharmaceutical solutions to tissues without flooding the bloodstream with high concentrations of drug. This is especially advantageous for drugs that have toxic side effects and that require high localized levels for therapeutic efficacy.

Fourth, due to the flexibility in the size of the infusion chamber that can be created, the single balloon infusion catheters of the invention also permit infusion of solutions into vessels having significant branching without loss of infusate due to run-off. Lastly, the single balloon flow-through catheters of the invention permit infusion therapy for extended periods of time without causing significant ischemia stasis or thrombosis downstream of the balloon.

The catheters of the invention find a wide variety of uses. In addition to being useful for the infusion of pharmaceutical agents useful to treat cardiovascular diseases, the catheters of the invention are also useful for infusing a wide variety of agents, including cancer therapeutic agents, antibiotics, agents affecting thrombosis, radiocontrast media, and radionuclear imaging preparations into a patient's vasculature. Furthermore, while the preferred embodiments have been described by illustrating the use of the catheters to locally deliver therapeutic agents into a patient's vasculature, it is to be understood that the catheters described herein may be utilized in virtually any catheterization circumstance, including genito-urinary catheterization, gastrointestinal catheterization and perfusion involving the middle or inner ear.

Although the present invention has been described in terms of specific embodiments and applications, persons skilled in the art can, in light of this teaching, generate additional embodiments without exceeding the scope or departing from the spirit of the claimed invention. The specific materials comprising the various elements of the catheters, for example, should not be construed as a limiting factor. Accordingly, it is to be understood that the drawings and descriptions in this disclosure are proffered to facilitate comprehension of the invention and should not be construed to limit the scope thereof.

What is claimed is:

1. A single balloon infusion catheter comprising:
    an elongated flexible shaft having a distal end and a proximal end and defining an inflation lumen extending from the proximal end of the shaft towards the distal end of the shaft;
    a balloon mounted on the distal end of the shaft, the inflation lumen being in communication with the balloon, the balloon including means for providing an infusion chamber between the balloon and an inner wall of a patient's vasculature when the balloon is inflated; and
    an infusion outlet defined by said catheter in a location communicating with said infusion chamber.

2. The catheter of claim 1, further comprising blood perfusion means for permitting blood flow past the balloon when the balloon is inflated.

3. The catheter of claim 1, wherein the shaft further defines an infusion lumen extending from the proximal end of the shaft to the distal end of the shaft, said infusion lumen communicating with the infusion outlet.

4. The catheter of claim 1, wherein the shaft further defines a guidewire lumen extending from the proximal end of the shaft to the distal end of the shaft.

5. The catheter of claim 1, wherein the balloon defines a plurality of said infusion outlets.

6. The catheter of claim 1, wherein said means for providing an infusion chamber comprises at least two annular non-inflatable spacers that contact an inner wall of the patient's vasculature when the balloon is inflated.

7. A single balloon infusion catheter comprising:
    an elongated flexible shaft having a distal end and a proximal end and defining an inflation lumen extending from the proximal end of the shaft towards the distal end of the shaft;
    a balloon mounted on the distal end of the shaft, the inflation lumen being in communication with the balloon, the balloon having at least two non-inflatable annular spacers that contact an inner wall of a patient's vasculature when the balloon is inflated, providing an infusion chamber between the balloon and the patient's vasculature; and
    an infusion outlet defined by said catheter in a location communicating with said infusion chamber.

* * * * *